(12) United States Patent
Bauer et al.

(10) Patent No.: US 8,955,308 B2
(45) Date of Patent: Feb. 17, 2015

(54) METHOD FOR OPERATING A REDUCING AGENT TANK AND MOTOR VEHICLE IN WHICH THE METHOD IS CARRIED OUT

(75) Inventors: Peter Bauer, Siegburg (DE); Jan Hodgson, Troisdorf (DE)

(73) Assignee: EMITEC Gesellschaft fuer Emissionstechnologie mbH, Lohmar (DE)

( * ) Notice: Subject to any disclaimer, the term of this patent is extended or adjusted under 35 U.S.C. 154(b) by 46 days.

(21) Appl. No.: 13/609,607

(22) Filed: Sep. 11, 2012

(65) Prior Publication Data

US 2013/0255234 A1 Oct. 3, 2013

Related U.S. Application Data

(63) Continuation of application No. PCT/EP2011/053492, filed on Mar. 8, 2011.

(30) Foreign Application Priority Data

Mar. 11, 2010 (DE) .......................... 10 2010 011 151

(51) Int. Cl.
 *F01N 3/00* (2006.01)
 *F01N 3/20* (2006.01)
 (Continued)

(52) U.S. Cl.
 CPC .............. *F01N 3/208* (2013.01); *F01N 3/2066* (2013.01); *F01N 13/008* (2013.01);
 (Continued)

(58) Field of Classification Search
 CPC ...... G01N 27/02; F01N 11/00; G01F 23/0076
 USPC ........................................................ 60/286
 See application file for complete search history.

(56) References Cited

U.S. PATENT DOCUMENTS

| 4,897,597 A * | 1/1990 | Whitener ....................... 324/693 |
| 6,994,589 B2 | 2/2006 | Schliese |

(Continued)

FOREIGN PATENT DOCUMENTS

| DE | 19743302 C1 | 2/1999 |
| DE | 19842484 A1 | 12/1999 |

(Continued)

OTHER PUBLICATIONS

English Translation of DE19842484 (Applicant IDS reference).*

(Continued)

*Primary Examiner* — Thomas Denion
*Assistant Examiner* — Anthony Ayala Delgado
(74) *Attorney, Agent, or Firm* — Laurence A. Greenberg; Werner H. Stemer; Ralph E. Locher

(57) ABSTRACT

A method for operating a tank for reducing agent, in particular aqueous urea solution, having a sensor with a first electrical contact and a second electrical contact, includes initially determining a conductance value for liquid reducing agent, a conductance value for frozen reducing agent and a conductance value for air in steps a.1) to a.3. A voltage is then applied between the first electrical contact and the second electrical contact in step b. A conductance value between the first electrical contact and the second electrical contact is then determined in step c. The conductance value determined in step c) is then compared to the conductance values determined in steps a.1) to a.3) and a determination is made as to if liquid reducing agent, frozen reducing agent, or air is present in step d). A motor vehicle in which the method is carried out, is also provided.

11 Claims, 4 Drawing Sheets

(51) Int. Cl.
  *F01N 13/00* (2010.01)
  *G01F 23/24* (2006.01)
  *F24H 9/20* (2006.01)
  *G01N 27/02* (2006.01)
  *B01D 35/027* (2006.01)

(52) U.S. Cl.
  CPC ............... *G01F 23/242* (2013.01); *F01N 3/20* (2013.01); *F24H 9/2007* (2013.01); *G01N 27/02* (2013.01); *B01D 35/027* (2013.01); *F01N 2610/10* (2013.01); *F01N 2610/1406* (2013.01); *F01N 2900/1806* (2013.01); *Y02T 10/24* (2013.01)
  USPC .................. 60/286; 60/273; 60/287; 324/693

(56) References Cited

U.S. PATENT DOCUMENTS

| | | | |
|---|---|---|---|
| 7,647,767 | B2 | 1/2010 | Osaku et al. |
| 7,912,360 | B2 | 3/2011 | Gschwind |
| 2006/0103393 | A1 | 5/2006 | Stahlmann et al. |
| 2009/0090178 | A1* | 4/2009 | Sasanuma et al. ............... 73/295 |
| 2009/0288734 | A1* | 11/2009 | Barcin et al. .................... 141/95 |
| 2010/0236243 | A1 | 9/2010 | Lolas et al. |
| 2011/0155262 | A1 | 6/2011 | Ante et al. |
| 2011/0210836 | A1 | 9/2011 | Baumeister |
| 2012/0111870 | A1 | 5/2012 | Hodgson et al. |

FOREIGN PATENT DOCUMENTS

| | | |
|---|---|---|
| DE | 198 41 770 A1 | 4/2000 |
| DE | 10047594 A1 | 4/2002 |
| DE | 10128301 A1 | 1/2003 |
| DE | 20 2006 010 615 U1 | 10/2006 |
| DE | 10 2008 031 645 A1 | 1/2010 |
| DE | 10 2008 056 860 A1 | 5/2010 |
| DE | 102009009711 A1 | 8/2010 |
| DE | 102009001736 A1 | 9/2010 |
| DE | 102009030674 A1 | 12/2010 |
| EP | 1 662 103 A1 | 5/2006 |
| WO | 0227280 A2 | 4/2002 |
| WO | 2010/000824 A1 | 1/2010 |
| WO | 2010000827 A1 | 1/2010 |

OTHER PUBLICATIONS

International Search Report of PCT/EP2011/053492, Dated May 13, 2011.

* cited by examiner

METHOD FOR OPERATING A REDUCING AGENT TANK AND MOTOR VEHICLE IN WHICH THE METHOD IS CARRIED OUT

CROSS-REFERENCE TO RELATED APPLICATION

This is a continuation, under 35 U.S.C. §120, of copending International Application No. PCT/EP2011/053492, filed Mar. 8, 2011, which designated the United States; this application also claims the priority, under 35 U.S.C. §119, of German Patent Application DE 10 2010 011 151.1, filed Mar. 11, 2010; the prior applications are herewith incorporated by reference in their entirety.

BACKGROUND OF THE INVENTION

Field of the Invention

The invention relates to a method for operating and determining the fill level of a tank in which a (liquid) reducing agent, such as a urea-water solution, is stored, in particular for a mobile application in the automotive field. The invention also relates to a motor vehicle in which the method is carried out.

Exhaust-gas purification devices, into which a reducing agent is supplied for the reduction of certain exhaust-gas constituents, are known, in particular for mobile internal combustion engines in motor vehicles. It is, for example, possible for nitrogen oxide compounds (NOx) in the exhaust gas to be eliminated in a particularly effective manner if ammonia is supplied as reducing agent to the exhaust gas. Typical reducing agents such as, for example, ammonia are hazardous substances and therefore should not be stored in motor vehicles directly. Therefore, reducing agent is generally stored in the form of a reducing agent precursor in a separate tank as an additional operating fluid in the motor vehicle. A typical reducing agent precursor is, for example, urea. Urea is stored in the motor vehicle, for example, in the form of a 32.5% urea-water solution. A urea-water solution of that type is available, for example, under the trademark "AdBlue".

A urea-water solution of that type typically freezes at temperatures of −11° C. A device for delivering and/or dosing liquid reducing agent is then no longer capable of delivering the urea-water solution. Such low temperatures may occur in motor vehicles, in particular as a result of long standstill periods. It is desirable to be able to reliably determine whether liquid or frozen reducing agent is present in a tank for reducing agent. Merely for the sake of completeness, it is pointed out at this juncture that the expression "reducing agent" should also be understood to include reducing agent precursors (such as, in particular, aqueous urea).

Furthermore, the consumption of reducing agent is generally low. The consumption of reducing agent is typically approximately 0.5% to 10% of the fuel consumption of an internal combustion engine. It is therefore sought to provide a simple and inexpensive sensor configuration for fill level determination. A complex continuous fill level determining method is generally not required. At the same time, however, high demands are placed, in particular, on the determination of a reserve fill level, so as to always ensure the desired purification action of the exhaust-gas treatment system.

SUMMARY OF THE INVENTION

It is accordingly an object of the invention to provide a method for operating and determining the fill level of a reducing agent tank with a fill level determining device and a motor vehicle in which the method is carried out, that overcome the hereinafore-mentioned disadvantages and at least partially solve the highlighted technical problems of the heretofore-known methods and vehicles of this general type.

With the foregoing and other objects in view there is provided, in accordance with the invention, a method for operating a tank having a sensor with a first electrical contact and a second electrical contact. The method comprises at least the following steps:
 a.1) defining a conductance value for liquid reducing agent;
 a.2) defining a conductance value for frozen reducing agent;
 a.3) defining a conductance value for air;
 b) applying a voltage between the first electrical contact and the second electrical contact;
 c) detecting a conductance value between the first electrical contact and the second electrical contact; and
 d) comparing the conductance value detected in step c) with the conductance values defined in steps a.1) to a.3) and determining if liquid reducing agent, frozen reducing agent or air is present.

The method according to the invention will in part also be illustrated in conjunction with various embodiments of a tank for a reducing agent. The tank is accordingly suitable, in particular, for carrying out the method according to the invention, and will therefore be described first for illustrative purposes. The tank has a tank wall, an interior which is at least partially delimited by the tank wall and a sensor with a first electrical contact and a second electrical contact disposed on the tank wall. The first electrical contact and the second electrical contact are connected in an electrically conductive manner to the interior, extend through the tank wall from the interior to an outer side of the tank wall and are disposed at a first spacing of less than 5 cm [centimeters] from one another. The first electrical contact and the second electrical contact are preferably disposed at a first spacing of less than 3 cm, particularly preferably even less than 2 cm, form one another. That the first electrical contact and the second electrical contact extend through the tank wall means substantially that the first electrical contact and the second electrical contact produce an electrical connection from the interior of the tank to an outer side of the tank.

At least the first electrical contact and/or the second electrical contact may be formed by a metallic pot which is disposed in the tank. Such a pot may, for example, be a housing for a dosing device which serves for delivering reducing agent out of the tank. At least the first electrical contact and/or the second electrical contact may furthermore be formed by an extraction line, a return line, an extraction point or an outlet line for the dosing device. An extraction line, a return line, an extraction point and an outlet line are various lines through which the dosing device for delivering the reducing agent is connected to the interior of the tank. It is necessary for the functioning of the tank that the first electrical contact be electrically insulated with respect to the second electrical contact in order to ensure that electrical properties of the reducing agent in the tank can be determined.

The tank wall is preferably produced from plastic. The electrical contacts which together form the sensor are preferably cast into the tank wall. It is additionally possible, if appropriate, for at least one sealing element to be jointly cast into the tank wall. The sealing element seals off the electrical contacts with respect to the tank wall. The electrical contacts are preferably in the form of metallic pins. The metallic pins may, if appropriate, have a surface structure which promotes the sealing of the tank wall against the metallic pins. It is also possible, if appropriate, for a groove to be formed into the metallic pins. A sealing element, such as for example an O-ring seal, engages into the groove. If appropriate, the metallic pins may also have a bulged portion through which improved sealing of the pins in the tank wall is attained.

It is possible, firstly, for the electrical contacts to extend in each case individually through the tank wall. It is, however, also possible for the metallic pins to be disposed in a common sealing element and for the sealing element as a whole to be embedded into the tank wall or extend through the tank wall.

It is basically possible for a plurality of such sensors to be provided, but it is preferable for only a single sensor to be provided on a tank of this type. A plurality of such sensors may be provided in a tank, for example in order to be able to carry out a measurement reliably at least at one of the sensors in the case of low fill levels and/or when the tank is in an oblique position. In the case of low fill levels, an oblique position of the tank may have the result that no reducing agent is present at a sensor even though reducing agent would actually still be present at the sensor, if the tank were in a horizontal alignment, when a certain reducing agent quantity is stored in the tank. The error rate of the fill level measurement system can consequently be reduced in this way.

Where "electrical contacts" are referred to herein, this means the first electrical contact and the second electrical contact. This terminology is not intended to express that the first electrical contact and the second electrical contact must then always be of identical construction and, in fact, this is intended to express that at least one of the contacts may be constructed in this way. This applies correspondingly to other generalizations, for example to pins, seals, etc.

A particularly preferred embodiment of the tank is provided if the sensor is disposed on a tank base or bottom. A fill level in the tank can be determined through the use of the sensor explained above. In particular, it is possible to determine a reserve fill level because a discrete fill level determination is possible through the use of a measurement between the two electrical contacts. For this purpose, a voltage is applied to the electrical contacts and an electrical resistance (or a conductance value=reciprocal of the resistance) between the electrical contacts is determined. A conclusion can be drawn as a function of the measurement value as to whether and/or how much reducing agent is present in the first spacing between the two electrical contacts of the sensor and/or what state of aggregation (for example liquid or frozen) the reducing agent is in.

The reserve fill level in the tank is determined preferably in the vicinity of the tank base because in the vicinity of the tank base, the two electrical contacts may be disposed at the same level. Furthermore, a configuration in the vicinity of the tank base permits a particularly advantageous determination of a residual volume. Specifically, a residual volume generally constitutes only an areal coverage of the tank base. Also, a sensor disposed in the tank base may be disposed in the center of the tank base. In this way, the sensor is made less sensitive to sloshing movements in the tank and/or to a possible oblique position of the tank, because sloshing movements and/or an oblique position cause a (particularly pronounced) change in the fill level specifically at a distance from the center, at the edge close to the tank side walls. Furthermore, tanks in motor vehicles are, if appropriate, installed so as to allow access to the tank only from below. The sensor is therefore particularly easily accessible, for example for maintenance work if it is disposed in the tank base. It is particularly preferable for the electrical contacts to project from the tank base into the tank interior with a first length of at most 5 cm [centimeters], preferably between 0.2 cm and 2 cm, particularly preferably between 0.5 cm and 1 cm. In the region of the first length, the electrical contacts are preferably blank, that is to say in particular not electrically insulated. Consequently, an electrical current can pass from the electrical contacts into the reducing agent over the entirety of the first length.

In a further advantageous embodiment, the sensor may also be disposed on a tank wall. It is, in particular, also possible for a plurality of sensors, for example between two sensors and ten sensors, to be distributed over a circumference of the tank at a certain level. It is thus possible, through the use of the multiplicity of sensors, to perform monitoring of the tank, wherein even in the case of an oblique position and in the event of sloshing movements in the tank, at least one of the sensors is suitable for a representative measurement.

The fill level signals determined by the individual sensors may be evaluated in a suitable controller in order to obtain a corrected fill level signal. For example, a mean value may be formed from the individual fill level signals in order to determine whether or not a reserve level to be monitored has been undershot. In a further structural variant, a decision as to whether or not a reserve level has been undershot may also be made by determining the ratio of the number of sensors at which reducing agent is present to the total number of sensors provided. If, for example, more than half of the sensors signal that the reserve level has been undershot, it can be decided that the reserve level has been undershot. A statistical evaluation of the fill level signals of the plurality of sensors, for example through the use of principal component analysis, is also possible.

In a further advantageous embodiment, a shoulder with a reserve height is disposed in the region of the electrical contacts. The shoulder insulates the electrical contacts up to the reserve level. In this way, in the case of electrical contacts disposed in the tank base, a reserve level fill quantity is precisely defined.

It is furthermore advantageous for the tank to have a heater and for the heater to be disposed at a spacing of less than 50 cm [centimeters] from the sensor. The second spacing is preferably less than 20 cm and particularly preferably less than 10 cm. For this purpose, the heater is disposed, in particular, in the vicinity of the tank base. The heater is, in particular, a regulable electric heater (for example having at least one element from the group including heating wire, heating foil, PTC element, cooling water heating configuration). In the case of a cooling water heating configuration, it is preferable for a heating coil to be guided through the tank. The cooling water or coolant heated by the internal combustion engine flows through the heating coil and dissipates heat energy to the reducing agent in the tank.

If the reducing agent in the tank has completely frozen, a cavity in the frozen reducing agent (a so-called "ice cavity") forms in the vicinity of the tank base during the operation of a heater. There is a (partially) liquid reducing agent present in the cavity. The size of the ice cavity can be determined through the use of a sensor which is disposed at a defined second spacing from the heater and which has two electrical contacts. Firstly, a sensor composed of two electrical contacts can determine, through a conductance value measurement, whether liquid reducing agent or frozen reducing agent is present at the sensor. Furthermore, it is possible to draw a conclusion therefrom as to a temperature distribution in the tank. It is additionally possible to take the energy introduced into the tank by the heater into consideration in order to determine the temperature distribution in the tank.

Furthermore, it is proposed that a temperature sensor be attached at least to one electrical contact on the outer side of the tank wall. Electrically conductive contacts generally have good thermal conductivity due to their inherent electrical conductivity. By contrast, the tank wall, which is preferably produced from plastic, has poor thermal conductivity. The electrical contacts thus constitute a thermal bridge through the tank wall. This can be utilized to attach a temperature sensor to the outside of a tank wall, and to determine a temperature on the inner side of the tank wall or in the interior of the tank by using the temperature sensor and one of the two electrical contacts. The possibilities for determining a temperature distribution in the tank are further improved through the use of a sensor of this type.

With regard to the method according to the invention, it is firstly pointed out that electrical variables are referred to herein at all times (conductance value, voltage, contact, resistance ... ). Furthermore, it should be noted that steps a.1), a.2) and/or a.3) need not be carried out every time a determination of the fill level and/or of the state of aggregation is performed, but rather if appropriate need be carried out only once. The corresponding conductance values may then be stored (permanently) as guide values or as a tolerance range and taken into consideration as a reference in step d) for the conductance values presently measured in step c). Consequently, the conductance values from steps a.1), a.2) and a.3) may also be referred to as reference conductance values. The conductance values of liquid reducing agent and frozen reducing agent generally differ in such a way that, as a result of a determination of the conductance value, it can be inferred whether liquid reducing agent or frozen reducing agent is present. Air is a highly effective electrical insulator in relation to reducing agent, so that on the basis of a conductance value determination between the two electrical contacts, air can also be identified. The conductance value of frozen reducing agent and the conductance value of air are similar. In particular, it can be ascertained that the difference between the conductance value of frozen reducing agent and the conductance value of air is considerably smaller than the differences between the conductance value of air and the conductance value of liquid reducing agent and between the conductance value of frozen reducing agent and the conductance value of liquid reducing agent.

In accordance with another particularly advantageous mode of the invention, a temperature sensor is provided on the tank and a temperature measured through the use of the temperature sensor is also taken into consideration in step d). As already explained, the conductance values of frozen reducing agent and of air differ from one another to a lesser extent than they differ from the conductance value of liquid reducing agent. For this reason, it may be advantageous if a measured temperature is jointly taken into consideration in step d) for the distinction as to whether air or frozen reducing agent is present. If the temperature lies above a threshold temperature of, for example, higher than −10° C. or preferably higher than −5° C. and particularly preferably higher than 0° C., frozen reducing agent can no longer be present, so that on the basis of the conductance value, a distinction need only be made between air and liquid reducing agent.

Furthermore, values measured in preceding method iterations may be jointly taken into consideration in step d). Additionally, in step d), it may be taken into consideration whether and/or to what extent a heater has been operated in a time interval before the execution of the method. For example, if frozen reducing agent was detected in a preceding method iteration and furthermore, in step d), a heater has been operated in order to thaw the reducing agent, it can be expected that liquid reducing agent will be detected before air is detected. A conductance value which is normally characteristic of air can thus be evaluated in step d) to mean that frozen reducing agent is present if it has not been possible in the meantime to detect liquid reducing agent.

In accordance with a further particularly advantageous mode of the invention, method steps a.1) to a.3) are carried out in advance and the conductance values of liquid reducing agent, frozen reducing agent and air are stored in a first memory, and then the conductance values of liquid reducing agent, frozen reducing agent and air are read out from the first memory for step d). The first memory may be provided in a control unit such as, for example, the engine controller of a motor vehicle.

A conductance value may be used which was measured at an earlier point in time as a reference for the conductance value of liquid reducing agent. The tank should with certainty have stored liquid reducing agent at that point in time. Whether or not this is the case can be determined through the use of a temperature sensor. If a temperature above a defined threshold temperature has been measured through the use of a temperature sensor positioned on or in the tank or on or in a dosing unit for reducing agent, it can be assumed with certainty that liquid reducing agent is present in the tank. Furthermore, it is also possible for steps a.1) to a.3) to be carried out in advance in a test setup. The conductance values may likewise be stored in a first memory from which they are read out during later operation for the execution of step d). The memory may in this case be a read-only memory which is non-rewritable.

The quality and the composition of reducing agent are not always exactly constant. As already stated, reducing agent is generally a 32.5 percent urea-water solution. Firstly, the urea content may vary slightly in such a solution. Secondly, there may be impurities in the solution. It is thus possible for the conductance values (in particular the conductance values of liquid reducing agent and frozen reducing agent) to vary slightly. Method steps a.1) to a.3) should therefore be carried out at least when the properties of the reducing agent could have (identifiably) changed. This should be performed, in particular, after the tank is refilled with reducing agent, because the reducing agent with which the tank is refilled may have different properties.

In accordance with an added advantageous mode of the invention, in step b), an alternating voltage, which alternates between a positive voltage value and a negative voltage value, is applied to the first electrical contact and to the second electrical contact. The alternating voltage is preferably rectangular. It is furthermore preferable for the alternating voltage to be symmetrical. This means that the negative voltage component and the positive voltage component correspond in form and magnitude. It is thus possible to prevent deposits from forming on one of the two contacts as a result of electrolysis.

In accordance with an additional advantageous mode of the invention, the tank has a heater and the method is expanded to include the following steps:

e.1) activating the heater if, in step d), it has been determined that frozen reducing agent is present;

e.2) deactivating the heater if, in step d), it has been determined that air is present.

If an ice cavity in the frozen reducing agent is formed around a heater in the tank, liquid reducing agent should be present in the ice cavity in order to ensure that the heat from the heater can be transported to the remaining frozen reducing agent. By contrast, air in the ice cavity constitutes a thermal insulator. If there is no connection of liquid reducing agent between the heater and the remaining frozen reducing agent in the ice cavity, further operation of the heater is generally not expedient because the heat energy output by the heater can no longer pass efficiently to the frozen reducing agent. In the case of a PTC heater (PTC: positive temperature coefficient), such a situation can be identified by monitoring the electrical current consumption of the heater. If the heater already exhibits reduced electrical current consumption shortly after activation, an ice cavity is present. In the case of a resistance heater, such a situation can be identified by determining the ratio of the current consumption to the heating voltage. If the ratio has decreased considerably, an ice cavity is present. For this reason, it is expedient for the heater to be deactivated if an insulating air layer has been detected in an ice cavity. In a further method implementation, the heater may also be operated with reduced power if air is present in the tank.

If frozen reducing agent is still present at the sensor in a corresponding embodiment of the tank, it is not important in this case whether an ice cavity filled with reducing agent or with air exists in the direct vicinity of the heater, because the second spacing between the heater and the sensor is selected in such a way that an ice cavity possibly present between the sensor and the heater is so small that adequate heat transport from the (two-dimensional) heater into the frozen reducing agent is possible despite the ice cavity. Specifically in the case of very small ice cavities, the capability of the air to transport heat from the heater to the frozen reducing agent is sufficient, so that the heater can remain activated.

The special advantages and embodiments highlighted with regard to the tank are applicable and transferable to the method according to the invention.

With the objects of the invention in view, there is concomitantly provided a motor vehicle, comprising an internal combustion engine with an exhaust-gas treatment device which has a dosing device for reducing agent. The dosing device has a tank as described herein and a controller, and the controller is set up or configured or programmed to carry out the method according to the invention.

Other features which are considered as characteristic for the invention are set forth in the appended claims, noting that the features listed individually in the claims can be combined with one another in any desired technologically expedient manner, thus highlighting further embodiments of the invention.

Although the invention is illustrated and described herein as embodied in a method for operating and determining the fill level of a reducing agent tank and a motor vehicle in which the method is carried out, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE INVENTION

Figure 1:
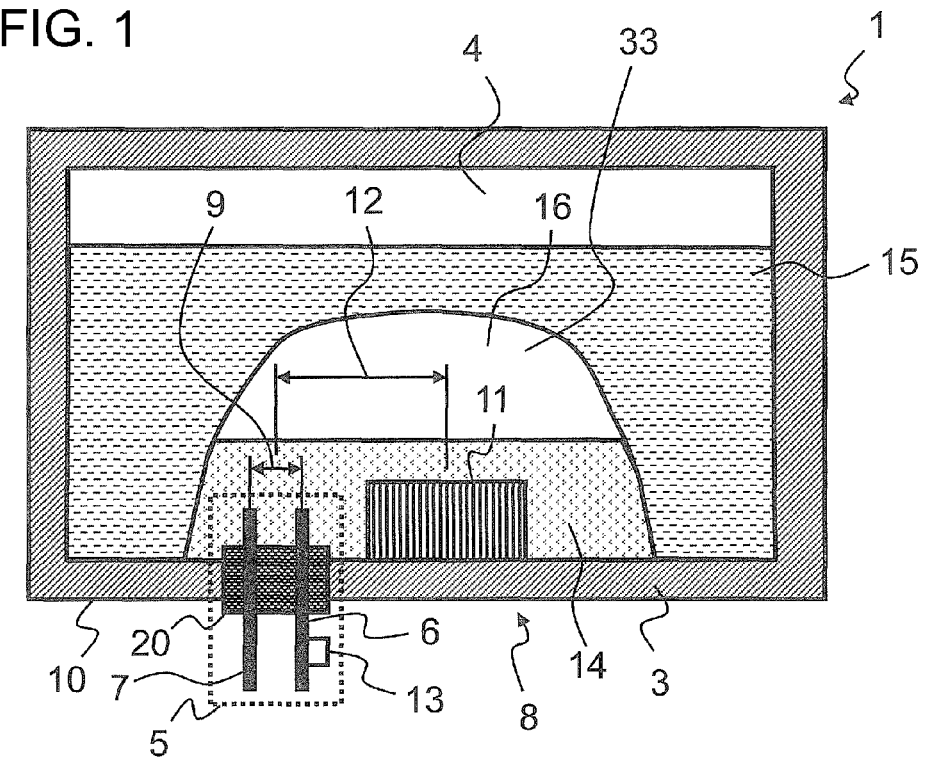
FIG. 1 is a diagrammatic, longitudinal-sectional view of a tank for reducing agent.

Referring now to the figures of the drawings in detail and first, particularly, to FIG. 1 thereof, there is seen a tank 1. The tank 1 has a tank wall 3 which delimits an interior 4. An ice cavity 33 is formed in frozen reducing agent 15 which is situated in the tank 1. The ice cavity 33 is filled partially with air 16 and partially with liquid reducing agent 14 (which in this case, in particular, is a urea-water solution). The ice cavity 33 is formed around an (electrically regulable, two-dimensional) heater 11. The heater 11 is disposed on the tank wall 3 in the region of a tank base or bottom 10. A sensor 5 is situated at a second spacing 12 from the heater 11. The sensor 5 is likewise disposed in the tank wall 3, specifically in the tank base 10. The sensor 5 has a first electrical contact 6 and a second electrical contact 7. The first electrical contact 6 and the second electrical contact 7 are disposed at a first spacing 9 from one another and are lead through the tank wall 3 of the tank 1 with a seal 20. The temperature in the interior 4 of the tank 1 or the temperature of the reducing agent can be detected from an outer side 8 of the tank 1 through the use of a temperature sensor 13 fastened to the first electrical contact 6.

Figure 2:
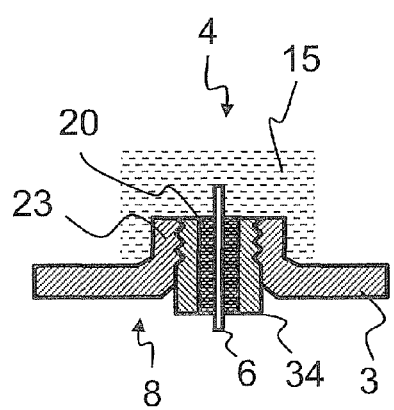
FIG. 2 is an enlarged, sectional view of a first structural variant for electrical contacts.

FIG. 2 shows an example of the way in which an electrical contact can extend through a tank wall 3. The tank wall 3 has an inwardly protruding portion 23 into which a threaded tube 34 is inserted. The first electrical contact 6 is disposed in the threaded tube 34 with a seal 20. The interior 4 of a tank which is, for example, filled with frozen reducing agent 15 is sealed off with respect to the outer side 8 through the use of the seal 20.

Figure 3:
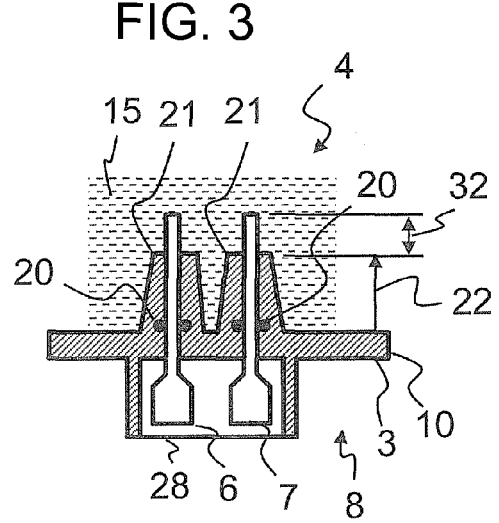
FIG. 3 is an enlarged, sectional view of a second structural variant for electrical contacts.

FIG. 3 shows a further example of the way in which a first electrical contact 6 and a second electrical contact 7 can extend through a tank wall 3. In this case, the tank wall 3 is penetrated in the region of the tank base 10. The first electrical contact 6 and the second electrical contact 7 are embedded into the tank wall 3 through the use of seals 20. The tank interior 4, which is filled with reducing agent 15, is thus sealed off with respect to an outer side 8. A protective frame 28, which is attached to the tank wall 3 on the outer side 8, protects the first electrical contact 6 and the second electrical contact 7. The protective frame 28 may be directly jointly provided during the production of the tank 1 so as to be in one piece therewith. The protective frame 28 may, for example, be integrally injection molded or integrally cast onto the tank 1. The protective frame 28 may also form a plug socket. A cable with a corresponding connecting plug may then be connected directly to the first electrical contact 6 and to the second electrical contact 7. The protective frame 28 then provides mechanical stability to the connection between the tank 1 and the connecting plug. In the interior 4, a respective shoulder 21 for each of the first electrical contact 6 and the second electrical contact 7 is provided on the tank wall 3 in the region of the first electrical contact 6 and of the second electrical contact 7. The shoulders 21 serve to define a reserve level 22 in the tank (the reserve level is the fill level in the tank when only the reserve volume of liquid reducing agent is present). The first electrical contact 6 and the second electrical contact 7 each project out of the shoulders 21 over a first length 32. Reliable electrically conductive contact between the reducing agent present in the interior 4 and the first electrical contact 6 and the second electrical contact 7 is thus ensured. The configuration according to FIG. 3 is suitable, in particular, for a configuration of the sensor in the tank base 10.

Figure 4:
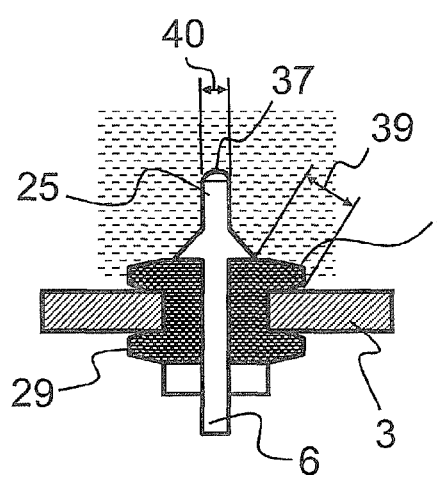
FIG. 4 is an enlarged, sectional view of a third structural variant for electrical contacts.

FIG. 4 shows a further example of the way in which an electrical contact can extend through a tank wall 3. In this case, the first electrical contact 6 is in the form of a rivet 25. The rivet 25 braces a rubber bushing 29 as a seal 20 against the tank wall 3.

Figure 5:
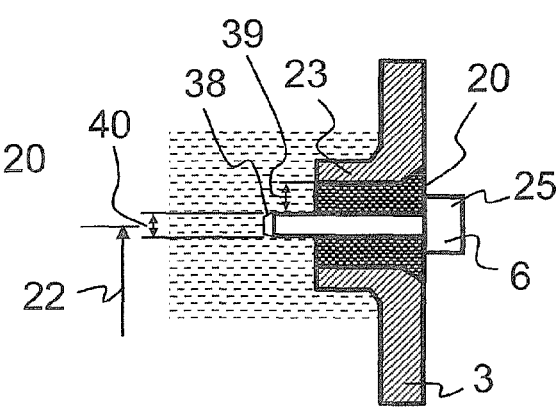
FIG. 5 is an enlarged, sectional view of a fourth structural variant for electrical contacts.

FIG. 5 shows a first electrical contact 6 which is inserted into a side region of a tank wall 3 (tank side wall). In this case, too, only the first electrical contact 6 is shown as an example. The first electrical contact 6 is likewise in the form of a rivet 25 which is inserted through the use of a seal 20 into an inwardly protruding portion 23 of the tank wall 3. A reserve level 22 is defined in this case by the configuration of the first electrical contact 6 in the tank wall 3 and not by the height of a shoulder 21. The further that the tank base is positioned from the first electrical contact 6 or the electrical contacts on the tank wall 3, the higher the reserve level 22.

FIGS. 4 and 5 furthermore illustrate particularly preferred shapes of a first electrical contact 6. The shapes are selected in such a way that no deposits and/or accumulations of reducing agent and/or reducing agent residues can occur in or on the first electrical contact 6, or that such deposits and/or accumulations are avoided to the greatest possible extent. Such deposits may lead to a short circuit between the first electrical contact 6 and the tank wall 3 and/or a short circuit between the first electrical contact 6 and the second electrical contact 7. In particular, the end of the first electrical contact 6 may have a correspondingly suitable construction in this case. FIG. 4 shows, for example, a lens shape 37 for the end of the first electrical contact 6. FIG. 5 shows a first electrical contact 6 which has a preferably encircling bevel 38 on the end thereof. The thickness 40 of the first electrical contact 6 may also be selected appropriately. The thickness 40 is preferably at least 0.5 mm [millimeters], preferably at least 1 mm and particularly preferably at least 2 mm.

Furthermore, in order to prevent a short circuit as a result of deposits and/or accumulations, it is important for the insulation of the first electrical contact 6 with respect to the tank wall 3 and with respect to a second electrical contact 7 to have an adequate width 39. A width 39 preferably means a shortest distance on the surface of the insulation from the tank wall 3 to the first electrical contact 6. In FIG. 4 and FIG. 5, the insulation is formed by the seal 20. The width 39 is preferably at least 0.5 mm [millimeters] and particularly preferably at least 1 mm.

These special embodiments proposed for the first electrical contact 6 are analogously transferable to a second electrical contact 7, which is however not separately illustrated in FIG. 4 and FIG. 5 for the sake of simplicity.

Figure 6:
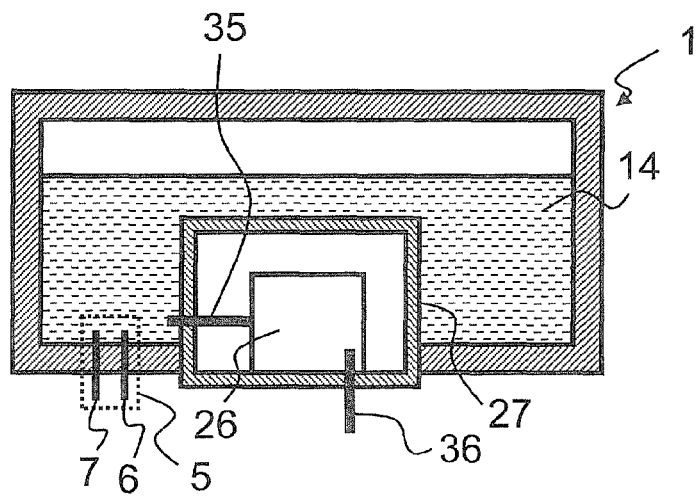
FIG. 6 is a longitudinal-sectional view of a tank having a temperature sensor.

FIG. 6 shows a further tank 1 with a sensor 5 which is formed with a first electrical contact 6 and a second electrical contact 7. The tank 1 has a metallic pot 27 in which a delivery unit 26 for transporting and/or dosing the reducing agent is disposed. Through the use of the delivery unit 26, the liquid reducing agent 14 can be discharged from the interior of the tank 1 through an extraction point 35. The delivery unit 26 may include, as parts, for example, a filter, a pump, a valve, transport lines, etc. which are jointly integrated in the metallic pot 27. The liquid reducing agent is supplied (if appropriate at elevated pressure) through an outlet line 36 from the delivery unit 26, for example, to a non-illustrated dispensing point or dosing point of an exhaust system.

Figure 7:
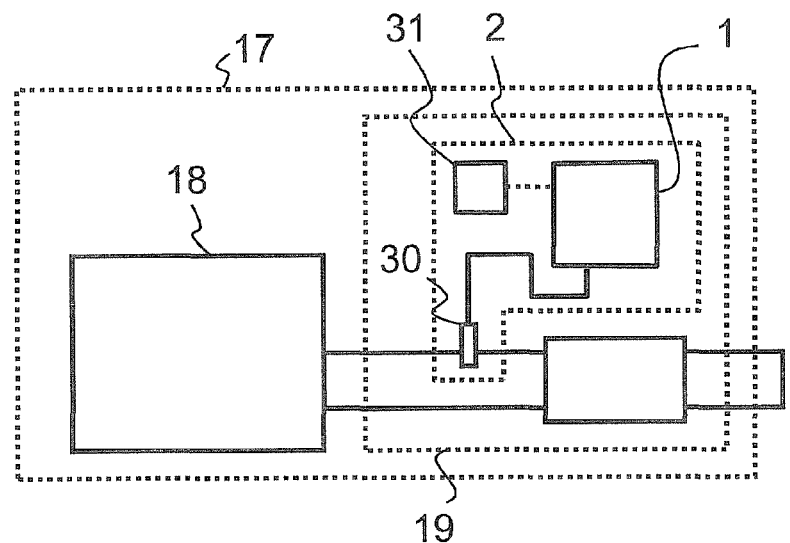
FIG. 7 is a longitudinal-sectional view of a motor vehicle having a tank.

FIG. 7 shows a motor vehicle 17 having an internal combustion engine 18 and an exhaust-gas treatment device 19. A dosing device 2, which has a tank 1, is provided in the exhaust-gas treatment device 19. Liquid reducing agent stored in the tank 1 can be dosed in predefined quantities through an injector 30 by using a delivery unit (which is preferably integrated in the tank) of the exhaust-gas treatment device 19.

Figure 8:
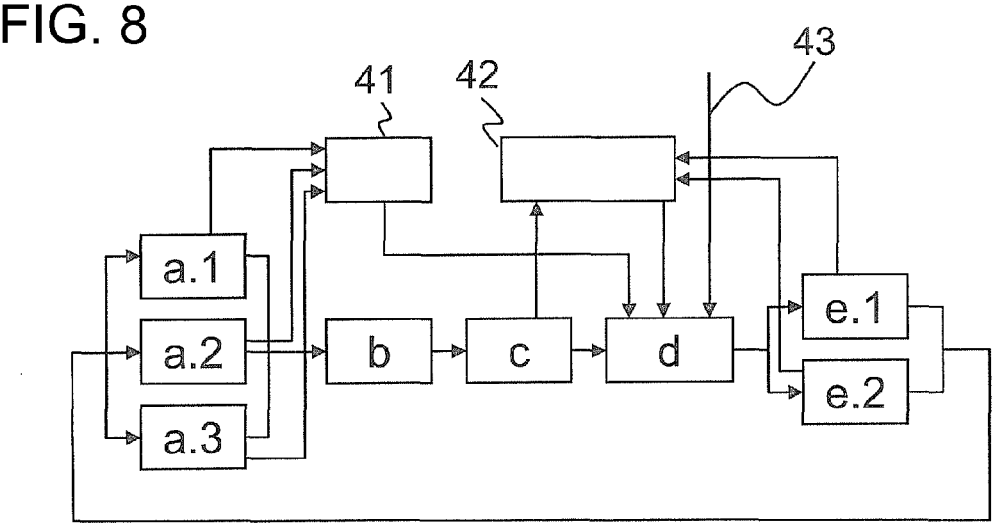
FIG. 8 is a flow diagram of the method according to the invention.

FIG. 8 shows a flow diagram of the method according to the invention. Method steps a.1) to a.3), b), c), d), e.1) and e.2) are shown. It can also be seen that the method can be carried out so as to be repeated (multiple times) in an iterative manner in the form of a loop, wherein the method steps a.1) to a.3) need not be carried out during every iteration of the method. Additionally illustrated is a first memory 41 in which conductance values determined in method steps a.1) to a.3) can be temporarily stored. The conductance values stored in the first memory 41 may be taken into consideration in step d). This is indicated by corresponding signal arrows in FIG. 8. Furthermore, conductance values measured in preceding iterations of the method in step c) and stored in a second memory 42 may be taken into consideration in step d). The storing of the conductance values is indicated by a signal arrow from step c) to the second memory 42. The consideration of the stored conductance value in step d) is indicated by the signal arrow from the second memory 42 to the step d). Temperature signals 43 and information, which is stored in the second memory 42, regarding the operation of a heater during a preceding time interval, may also be taken into consideration in step d). This, too, is indicated in each case by corresponding signal arrows. The first memory and/or the second memory may be provided in a control unit of a motor vehicle. Information regarding the operation of a heater may be gained, for example, from method steps e.1) and e.2). It can be identified when a heater has been operated on the basis of the activation process and the deactivation process of the heater. The information regarding the operation of a heater may, however, also be gained from the controller of the heater itself.

Figure 9:
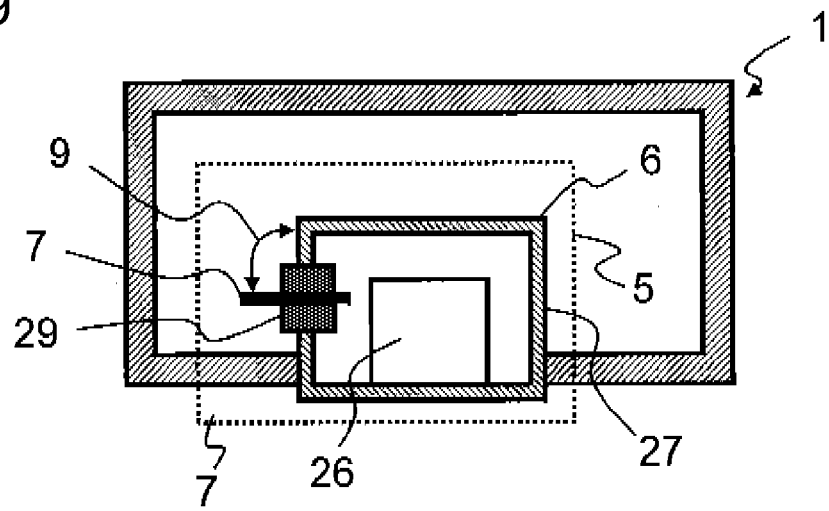
FIG. 9 is a longitudinal-sectional view of a tank with a fifth structural variant for electrical contacts.

FIG. 9 shows a fifth structural variant of a first electrical contact 6 and of a second electrical contact 7 for a tank 1 with a sensor 5. A metallic pot 27 is inserted into the tank 1. A delivery unit 26 for delivering reducing agent is disposed in the metallic pot 27. The metallic pot 27 forms the first electrical contact 6 of the sensor 5. The second electrical contact 7 is additionally provided. In the structural variant according to FIG. 9, the second electrical contact 7 extends through the metallic pot 27 and the second electrical contact is sealed off with respect to the metallic pot 27 through the use of a seal element. The seal element is, in the present case, in the form of a rubber bushing 29. Other structural variants of the seal element are, however, also conceivable. In a modified structural variant, the second electrical contact 7 may also extend through the tank wall 3 separately from the metallic pot 27. For example, the second electrical contact 7 may be disposed in the tank wall adjacent the metallic pot 27. The first electrical contact 6, which is in the form of a metallic pot 27, and the second electrical contact 7, preferably have a first spacing 9 of less than 5 cm [centimeters] from one another, as is the case with regard to the tank 1.

Figure 10:
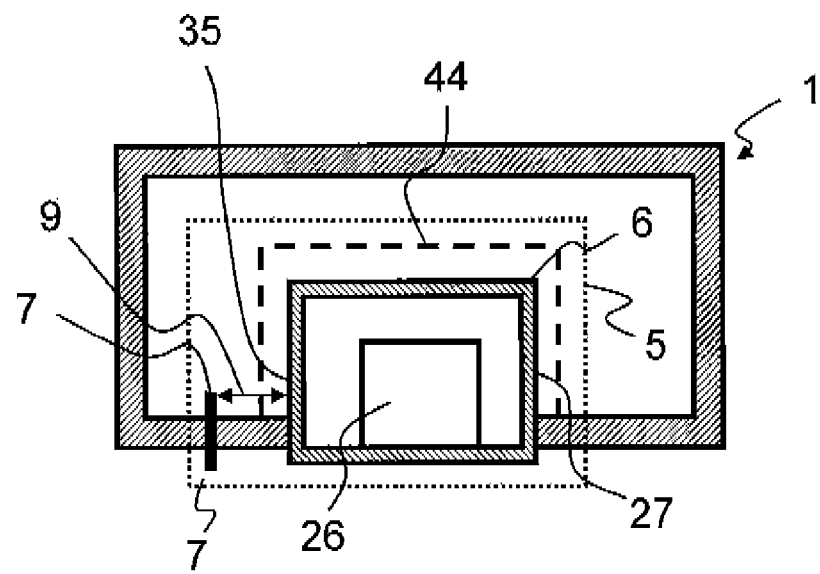
FIG. 10 is a longitudinal-sectional view of a tank with a sixth structural variant for electrical contacts.

FIG. 10 shows a sixth structural variant for a first electrical contact 6 and for a second electrical contact 7 for a tank 1 with a sensor 5. A metallic pot 27 with a delivery unit 26 is likewise inserted into the tank 1. In this case, too, the metallic pot 27 forms the first electrical contact 6. A filter 44 is disposed around the metallic pot 27. An extraction point 35 for reducing agent, through which reducing agent is transported from the tank 1 to the delivery unit 26, is disposed on the metallic pot 27. Reducing agent which passes from the tank 1 to the extraction point 35 is filtered by the filter 44. The second electrical contact 7 is disposed adjacent the metallic pot 27 with the filter 44. In this case, too, there is a spacing 9 of less than 5 cm [centimeters] between the first electrical contact 6 and the second electrical contact 7. The filter 44 is disposed between the first electrical contact 6 and the second electrical contact 7. This is, however, not disadvantageous for the measurement of the electrical properties of the reducing agent between the first electrical contact 6 and the second electrical contact 7.

A particularly advantageous method for operating a reducing agent tank with a fill level determining device has thus been specified herein.

The invention claimed is:

1. A method for operating a tank having a sensor with a first electrical contact and a second electrical contact, the method for operating the tank comprising the following steps:
   providing the tank with a heater;
   a.1) defining a conductance value for liquid reducing agent;
   a.2) defining a conductance value for frozen reducing agent;
   a.3) defining a conductance value for air;
   b) applying a voltage between the first electrical contact and the second electrical contact;
   c) detecting a conductance value between the first electrical contact and the second electrical contact; and
   d) comparing the conductance value detected in step c) with the conductance values defined in steps a.1) to a.3) and determining if liquid reducing agent, frozen reducing agent or air is present;
   e.1) activating the heater when it has been determined in step d) that frozen reducing agent is present; and
   e.2) deactivating the heater when it has been determined in step d) that air is present.

2. The method according to claim 1, which further comprises providing a temperature sensor on the tank, measuring a temperature with the temperature sensor on the tank, and taking the temperature measured with the temperature sensor on the tank into consideration in step d).

3. The method according to claim 1, which further comprises:
   carrying out steps a.1) to a.3) in advance;
   storing the conductance values of liquid reducing agent, frozen reducing agent and air in a memory; and
   reading out the conductance values of liquid reducing agent, frozen reducing agent and air from the memory for step d).

4. The method according to claim 1, which further comprises applying an alternating voltage, alternating between a positive voltage value and a negative voltage value, to the first electrical contact and the second electrical contact in step b).

5. A motor vehicle, comprising:
   an internal combustion engine;
   an exhaust-gas treatment device associated with said internal combustion engine and having a dosing device for reducing agent; and
   said dosing device having a controller configured to carry out the method according to claim 1.

6. The method according to claim 1, which further comprises:
   providing a controller;
   storing the conductance values of steps a.1) to a.3) on the controller; and
   carrying out step d) on the controller.

7. The method according to claim 1, wherein the first electrical contact and the second electrical contact are connected in an electrically conductive manner to an interior of the tank and extend through a tank wall from the interior to an outer side of the tank wall and are disposed at a first spacing of less than 5 cm from one another.

8. The method according to claim 7 wherein the first electrical contact and the second electrical contact are provided in a tank bottom and project from the tank bottom into the tank interior with a first length of at most 5 cm.

9. The method according to claim 1 wherein the method is repeated iteratively and wherein in step d) values measured during a preceding method iteration are taken in to consideration to determine whether liquid reducing agent, frozen reducing agent or air is present.

10. The method according to claim 1, wherein a conductance value for liquid reducing agent is defined in step a.1) as a conductance value which was measured at an earlier point in time when the tank had with certainty stored liquid reducing agent.

11. The method according to claim 1, wherein the heater is provided as a PTC heater.

* * * * *